(12) United States Patent
Miyasaka

(10) Patent No.: US 8,287,499 B2
(45) Date of Patent: Oct. 16, 2012

(54) SYRINGE AND CATHETER SET COMPRISING SAME

(75) Inventor: Susumu Miyasaka, Tokyo (JP)

(73) Assignee: Tyco Healthcare Group LP, Mansfield, MA (US)

( * ) Notice: Subject to any disclaimer, the term of this patent is extended or adjusted under 35 U.S.C. 154(b) by 53 days.

(21) Appl. No.: 13/048,174

(22) Filed: Mar. 15, 2011

(65) Prior Publication Data
US 2011/0270183 A1    Nov. 3, 2011

(30) Foreign Application Priority Data
Apr. 30, 2010   (JP) ................. 2010-105497

(51) Int. Cl.
*A61M 5/178* (2006.01)
(52) U.S. Cl. .................................. 604/168.01
(58) Field of Classification Search .......... 604/900, 604/168.01
See application file for complete search history.

(56) References Cited

U.S. PATENT DOCUMENTS

| | | | | |
|---|---|---|---|---|
| 4,617,941 A | * | 10/1986 | Ichikawa et al. | 600/578 |
| 4,660,569 A | * | 4/1987 | Etherington | 600/578 |
| 5,066,284 A | * | 11/1991 | Mersch et al. | 604/168.01 |
| 5,295,970 A | * | 3/1994 | Clinton et al. | 604/168.01 |
| 6,086,559 A | * | 7/2000 | Enk | 604/121 |
| 6,485,428 B1 | | 11/2002 | Enk | |
| 7,452,344 B2 | * | 11/2008 | Jorgensen et al. | 604/4.01 |
| 7,618,370 B2 | * | 11/2009 | Choi et al. | 600/371 |
| 7,654,963 B2 | * | 2/2010 | Egnelov et al. | 600/486 |
| 2003/0045813 A1 | * | 3/2003 | Cohen et al. | 600/573 |

FOREIGN PATENT DOCUMENTS

| | | |
|---|---|---|
| DE | 9208103 U1 | 3/1993 |
| EP | 0066702 B1 | 10/1986 |
| JP | 10-165509 A | 6/1998 |
| JP | 10165509 A * | 6/1998 |
| JP | 2000041938 | 2/2000 |

OTHER PUBLICATIONS

Machine Translation of Japanese Patent.*

* cited by examiner

Primary Examiner — Nicholas Lucchesi
Assistant Examiner — Diva K Chander
(74) Attorney, Agent, or Firm — Lisa E. Winsor, Esq.

(57) ABSTRACT

A syringe comprising a clear syringe barrel, a clear hollow plunge which can be pushed and pulled within the syringe barrel and is open at both ends, a gasket having a throughhole for providing communication between the inside of the plunger and the inside of the syringe barrel and provide a fluid tight seal with the syringe barrel, and a return-flow prevention mechanism which allows the fluid flowing into the plunger to flow in an outward direction from the inside of the plunger.

11 Claims, 3 Drawing Sheets

FIG. 1A
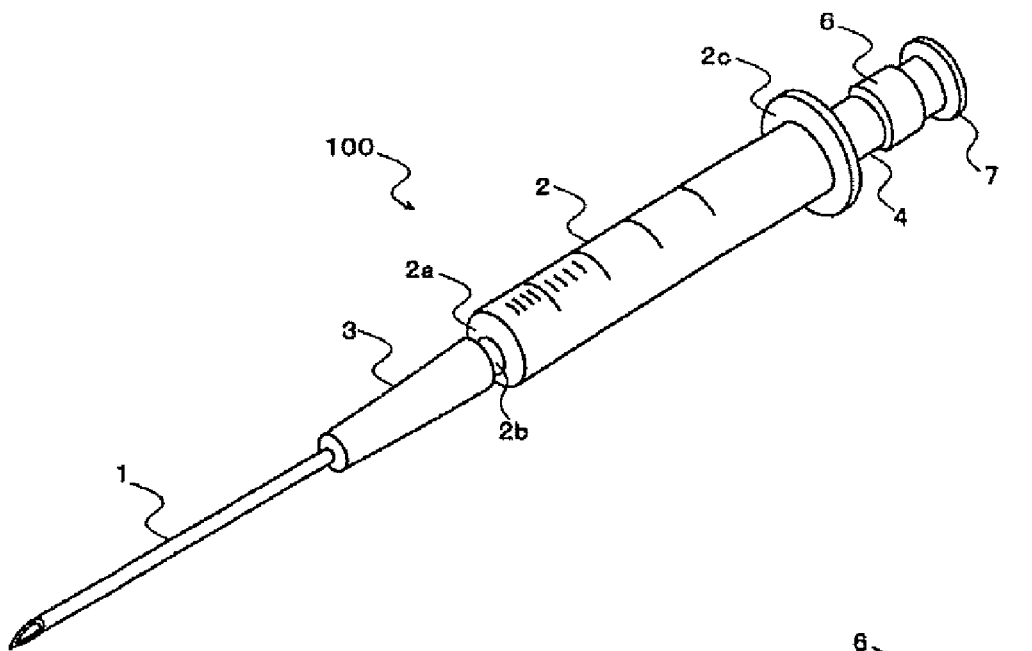
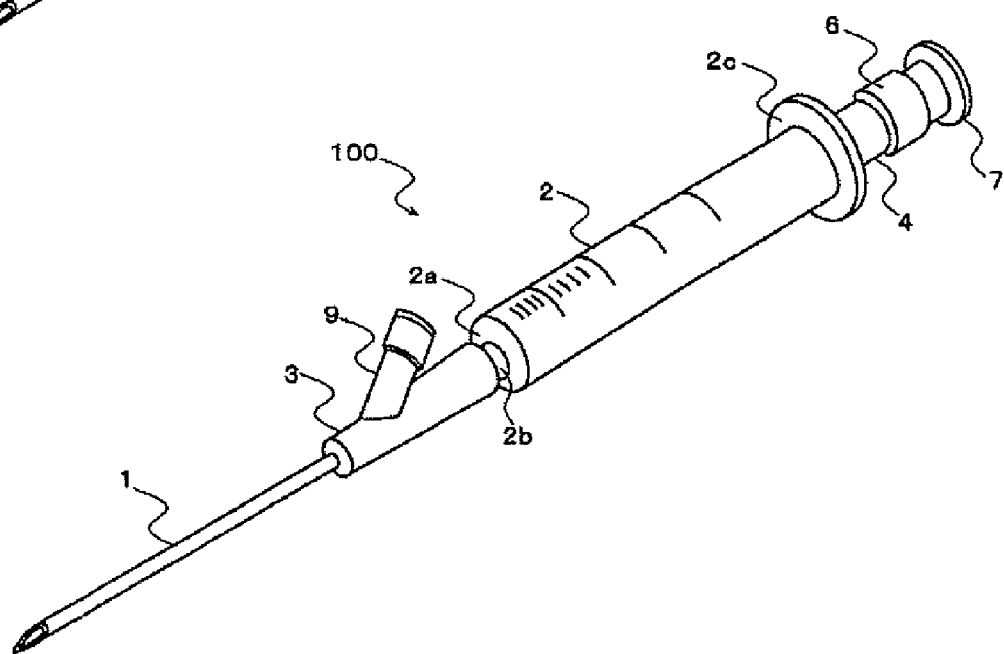
FIG. 1B

SYRINGE AND CATHETER SET COMPRISING SAME

RELATED APPLICATIONS

Foreign priority benefits are claimed under 35 U.S.C. §119 (a)-(c) of Japan Patent Application Number 2010-105497, filed Apr. 30, 2010, incorporated herein by reference in its entirety for all purposes.

BACKGROUND

1. Field of Invention

The present invention relates to a syringe which makes it possible to qualitatively visualize the pressure of fluids such as blood, and to a catheter set comprising said syringe.

2. Description of Related Art

When a catheter or guidewire is inserted into a blood vessel in a human or other body, the practitioner first of all ensures that the intended blood vessel (vein or artery) has been identified using a syringe which has a puncture needle fitted to the tip end. When a central venous (CV) catheter is made indwelling, for example, the subclavian vein or internal jugular vein is punctured using a cannula which can remain indwelling in a blood vessel (a puncture needle surrounded by a tube). When a blood vessel lying deep within the body is to be punctured, it is not possible to ascertain the position of the blood vessel or where it runs either visually or by palpation, and a practitioner such as a specialist physician will use his or her anatomical knowledge and experience to establish the puncture site and puncture direction. The only information at the practitioner's disposal when the blood vessel is identified is the slight feeling transmitted to the fingers when the tip of the puncture needle passes through the wall of the blood vessel and the return flow of blood.

Considering that the slight feeling when the tip of the puncture needle passes through the wall of the blood vessel is often eliminated by the pressure produced when the needle passes through the subcutaneous tissue and muscle which runs from the skin to the blood vessels, that this feeling is momentary and that it is easy to make mistakes on a subjective decision, the return flow of blood is considered to be the only reliable source of information. It is possible to establish whether the tip of the puncture needle attached to the end of the syringe is inside a blood vessel using the return flow (flash-back) of blood into the syringe barrel as a source of information.

The blood vessels lying deep inside the body are characterized by arteries and veins which run side-by-side, for example arteries lying close to or behind veins. The internal jugular vein runs parallel to the common carotid artery and the subclavian vein runs parallel to the subclavian artery, for example. The way the blood vessels run also varies from person to person, and it cannot be said that establishing a puncture site and puncture direction using the anatomical knowledge and experience of a practitioner is entirely without error. A practitioner therefore needs to correctly judge whether the blood vessel which has been punctured is a vein or an artery using information obtained from the return flow of blood.

In a medical setting it is also necessary to reliably establish in a short time that a vein rather than an artery has been punctured when a catheter or guidewire is inserted into a vein. That is to say, the patient needs to be treated swiftly and correctly in the medical setting for reasons of urgency and health, and it is important to be able to establish both quickly and accurately whether the blood vessel punctured by the puncture needle is indeed the intended blood vessel. It is nonetheless difficult to establish at a glance whether the blood vessel punctured by the puncture needle is the intended blood vessel, even for an experienced physician.

Standard methods of establishing whether the blood vessel which has been punctured is a vein or an artery from the return flow of blood involve determining any of the color of the aspirated blood, the oxygen saturation of the blood, or the blood pressure. When the blood vessel is identified by the color of the blood, it is possible to judge that it is an artery if the color of the blood is bright red and that it is a vein if the color of the blood is dark red. When the blood vessel is identified by the oxygen saturation of the blood, it is possible to judge that it is an artery if the oxygen saturation is high and that it is a vein if the oxygen saturation is low. When the blood vessel is identified by the blood pressure, it is possible to judge that it is an artery if the blood pressure is high and that it is a vein if the blood pressure is low.

When the blood vessel is identified by the color of the blood, it may be the case that the blood is not bright red, even if the blood vessel is an artery, because the patient's respiration becomes shallower when a general anaesthetic is in full effect, for example. Furthermore, if the oxygen partial pressure from an oxygen mask is high, the oxygen saturation in the blood also increases, and it may be the case that the blood comes close to being bright red even if the blood vessel is a vein. In addition, the color of the blood varies from person to person, and it is not the case that blood color is constant. For these reasons, the color of the blood is not fixed due to individual differences and the state of the patient at the time, and therefore the color of the blood is not a reliable indicator for identifying the blood vessel.

There is a correlation between the oxygen saturation and the color of the blood, and therefore when the blood vessel is identified by the oxygen saturation, the difficulties in making this determination in the case of blood color also apply to the determination in the case of oxygen saturation. Additional measuring equipment is also required in order to measure the oxygen saturation of the blood. Identifying the blood vessel by the oxygen saturation of the blood is therefore problematic in that is an impractical method because of the need to prepare separate measurement equipment, the complexity of the operation entailed by the measurement, and the time taken to obtain the measurement results, among other things.

On the other hand, it is possible to determine whether the blood vessel which has been punctured is a vein or an artery in a short time and with a greater degree of accuracy by utilizing the difference in blood pressure between arteries and veins. Technology has therefore been proposed for determining whether the blood vessel which has been punctured is an artery as, for example, in German Utility Model Application 920810, hereinafter DE 9208103. Technology has also been proposed which makes it possible to determine whether the blood vessel which has been punctured is a vein or an artery in a short time and with a greater degree of accuracy by utilizing the difference in blood pressure between arteries and veins as, for example, in Japanese Unexamined Patent Application Publication H10-165509 hereinafter JP 165509.

The technology disclosed in DE 9208103 involves attaching a display device 20 after the puncture has been made, rather than before or when the puncture is being made. When a blood vessel is punctured, the venous pressure is generally 2-8 mmHg, and therefore it is not possible to produce a return flow of blood unless there is negative pressure in the syringe when the puncture is being made. With the technology disclosed in DE 9208103, if it becomes necessary to provide negative pressure in the syringe and recheck whether the tip of the needle is in a blood vessel, the negative pressure is corrected once the device has been removed and then it is reattached, which leads to a complicated operation and procedure.

Furthermore, the operation to attach the display device 20 follows the confirmation of the blood vessel, and therefore there is a possibility that the subsequent attachment operation will cause the tip of the needle to become misaligned with the blood vessel which has at last been confirmed, and that the tip of the needle will be removed outside the blood vessel (for example, the needle will pass through the front wall or rear wall of the blood vessel, or the needle will come out from the blood vessel, etc.).

In addition, it is not generally possible to visually identify a blood vessel lying deep within the body, and therefore the operation to identify the blood vessel is normally repeated a number of times, since there is not really any expectation that the intended blood vessel can be identified in a single operation. If it proves impossible to identify the intended blood vessel, the blood etc. which has flowed into the syringe is discarded and the operation to confirm the blood vessel is carried out once again. However, with the technology disclosed in DE 9208103, there is a risk that the blood to be pushed out will head not towards the tip of the needle but towards a branch pipe 14, and even if only a small amount of blood etc. remains in the display device 20, it is necessary to prepare a new display device 20 once again. The technology disclosed in DE 9208103 is therefore not considered to be suitable for multiple blood vessel identification operations.

The technology disclosed in JP 165509 makes it possible to determine whether the blood vessel which has been punctured is a vein or an artery in a short time and with a greater degree of accuracy by utilizing the difference in blood pressure between arteries and veins. While this technology does have some advantages, there is a need to develop a syringe that is more easily used in practice, in addition to the need for further improvements in terms of usability, compactness, hygiene and cost etc.

The present invention has been devised in order to resolve the issues outlined above, and it aims to provide a syringe which utilizes the difference in pressure in fluids such as blood and which makes it possible to identify the target in a short time and with accuracy by qualitatively visualizing the pressure of said fluids; the invention also aims to provide a catheter set comprising such a syringe.

SUMMARY OF INVENTION

The syringe according to the present invention is provided with: a syringe barrel which is a cylinder whereof the inside can be seen and which has a bottom formed with a through-hole at a first end; a plunger which is provided inside the syringe barrel in such a way that it can be pushed and pulled, which is hollow inside and which is open at both ends; a gasket which is formed with an orifice for providing communication between the inside of the plunger and the inside of the syringe barrel, which is attached to the first end of the plunger, and whereof the outer peripheral surface comes into contact with the inner wall surface of the syringe barrel; and a return-flow prevention mechanism which allows the fluid flowing into the plunger from the first end of the plunger to flow in an outward direction from the inside of the plunger.

In the syringe according to the present invention, the opening pressure value of the return-flow prevention mechanism is set in accordance with the fluid flowing into the plunger.

In the syringe according to the present invention, the return-flow prevention mechanism consists of a cheek valve provided with a valve body and a housing in which the valve body is housed, and is detachably fitted to a second end of the plunger with the housing interposed.

In the syringe according to the present invention, a puncture needle constituting a fluid inflow port is detachably fitted to the bottom of the syringe barrel.

In the syringe according to the present invention, a hydrophobic filter is provided downstream of the return-flow prevention mechanism.

The catheter set according to the present invention comprises the syringe described above, and a catheter.

Other advantages, novel features and objects of the invention will become apparent from the following detailed description of the invention when considered in conjunction with the accompanying drawings, which are schematic and are not intended to be drawn to scale. In the FIG.s, each identical, or substantially similar component is represented by a single numeral or notation. For purposed of clarity, not every component is labeled in every FIG., nor is every component of each embodiment of the invention shown where illustration is not necessary to allow those of ordinary skill in the art to understand the invention.

BRIEF DESCRIPTION OF THE DRAWINGS

Preferred, non-limiting embodiments of the present invention will be described by way of example and with reference to the accompanying drawings, in which:

FIG. 1A is an oblique view showing the schematic structure of the syringe according to a mode of embodiment of the present invention;

FIG. 1B is an oblique view showing the schematic structure of the syringe with a side port according to another mode of the embodiment of the present invention;

DETAILED DESCRIPTION

The syringe according to the present invention comprises a hollow plunger and a return-flow prevention mechanism, and therefore the pressure difference in fluids flowing into the syringe barrel can be used in order to qualitatively visualize the pressure of said fluids, making it possible to identify a target in a short time and with accuracy. The syringe according to the present invention does not require a complicated structure or operation, and fluid identification operations can be carried out easily, which improves usability and makes the syringe more practical.

The syringe according to the present invention does not require a complicated structure, and the target can be identified in a short time and with accuracy.

The syringe according to the present invention can employ a conventional check valve and therefore it can be produced at low cost and in a compact manner.

The syringe according to the present invention can be fitted with a detachable needle and therefore a broad range of targets can be measured. If a puncture needle is fitted, for example, the blood flowing in a blood vessel deep inside the body can also be targeted.

The syringe according to the present invention may be provided with a filter downstream of the check valve and therefore it can respond to the requirements of health and safety.

The catheter set according to the present invention comprises the abovementioned syringe and therefore it demonstrates the same advantages as those of the syringe.

Modes of embodiment of the present invention will be described below in conjunction with the FIG.s.

Figure 2:
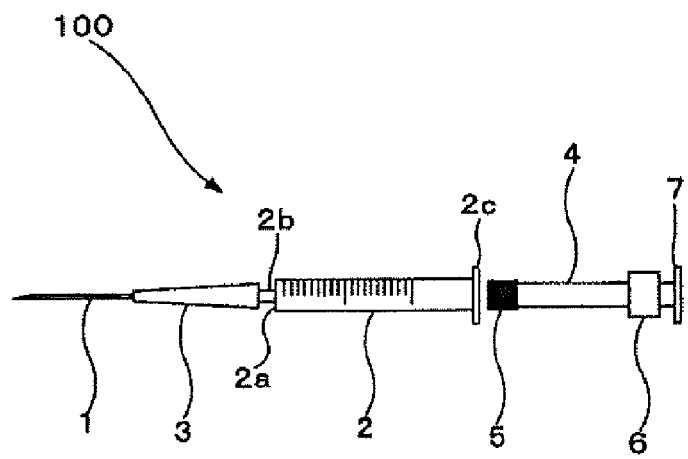
FIG. 2 is a schematic showing an example of the structure of the syringe according to a mode of embodiment of the present invention.
Figure 3:
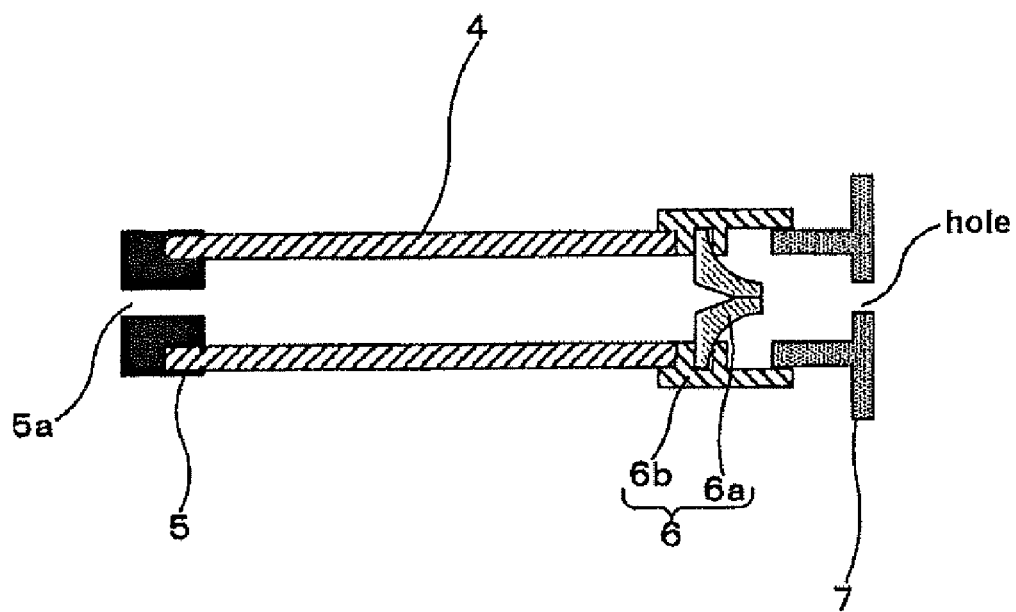
FIG. 3 is a schematic view in longitudinal section showing the cross-sectional structure of the plunger and the check valve.

FIG. 1A is an oblique view showing the schematic structure of a syringe 100 according to a mode of embodiment of the present invention. FIG. 2 is a schematic showing an example of the structure of the syringe 100. FIG. 3 is a schematic view in longitudinal section showing the cross-sectional structure of a plunger 4 and a check valve 6. The syringe 100 will be described in conjunction with FIGS. 1 to 3. The syringe 100 is a device which utilizes the difference in pressure of fluids such as liquids (e.g. blood) and gases (e.g. air), and which makes it possible to qualitatively visualize the pressure of the fluids. It should be noted that the actual size relationships between each of the structural components in the following FIGS., including FIG. 1, may be different to what is shown. Furthermore, FIG. 1B also shows the syringe 100 having a side port 9.

As shown in FIGS. 1A and 1B, the syringe 100 is used when a central venous (CV) catheter is made indwelling, for example, and it comprises at least: a puncture needle 1, a syringe barrel 2, a plunger 4, a gasket 5, and a check valve 6 which serves as the return-flow prevention mechanism. It should be noted that FIG. 1 shows the puncture needle 1, an adapter 3 for connecting the puncture needle 1 and the syringe barrel 2, and an operating part 7 for assisting in the operations to push and pull the plunger 4, but these only need to be used if necessary, and they are not essential components.

The puncture needle 1 is detachably fitted to a first end of the syringe barrel 2 by means of interlocking or screwing, with the adapter 3 interposed, and it serves to puncture a blood vessel in a human body etc., for example. The puncture needle 1 is formed with a through-hole inside through which fluid can be conducted, or a catheter or guidewire can pass. No particular limitation is imposed on the material from which the puncture needle is made, but metal or plastic should be used, for example. It should be noted that in the case of a syringe having a structure without the adapter 3, the puncture needle 1 should be directly attached to the syringe barrel 2 by interlocking or screwing.

The syringe barrel 2 is a clear, that is to say completely or partially transparent or translucent, cylinder whereof the inside syringe barrel cavity can be seen, with a shape having a bottom at the first end in which an attachment end (referred to below as the "bottom 2a") for the puncture needle 1 comprises a through-hole, and it communicates with the puncture needle 1 which is detachably fitted by way of the adapter 3. The syringe barrel 2 is made of a transparent synthetic resin, for example, and has a circular or polygonal (e.g. hexagonal or octagonal) cross-sectional shape. It should be noted that an example is given in this mode of embodiment in which the syringe barrel 2 has a circular cross-sectional shape.

Furthermore, a tubular part 2b to which the puncture needle 1 or adapter 3 can be detachably fitted by interlocking or screwing is formed so as to project in the centre of the bottom 2a of the syringe barrel 2. It should be noted that an example is given in this mode of embodiment in which the tubular part 2b is formed in the centre of the bottom 2a, but no particular limitation is imposed as to the position where the tubular part 2b is formed, and the tubular part 2b may be formed in a position which is offset from the centre of the bottom 2a. In addition, a stopper 2c is formed so as to project in the outer peripheral direction on the end edge of the syringe barrel 2 on the opposite side to the bottom 2a. It should be noted that the tubular part 2b may replace the puncture needle 1, depending on the target to be measured.

The plunger 4 is slidably disposed within the syringe barrel 2 and is provided so as to be able to be pushed and pulled inside the syringe barrel 2. The plunger 4 is made of a transparent or translucent synthetic resin, for example, and is formed with a hollow interior wherein the inside plunger cavity may be seen. Furthermore, both ends of the plunger 4 are open. That is to say, the plunger 4 allows fluid to pass through inside along an internal flow path, and the inside thereof can be seen. The plunger 4 is pushed and pulled in order to vary the pressure inside the syringe barrel 2.

Furthermore, the diameters of the two open ends of the plunger 4 may be narrower than the diameter of the internal flow path of the plunger 4. If the diameter of the first end of the plunger 4 (the tip end on the bottom 2a side) is narrower than the internal flow path of the plunger 4, the speed of the fluid flowing into the plunger 4 can be increased, and the inflow of fluid can be more easily confirmed. It should be noted that the gasket 5 is attached to the first end of the plunger 4 (the tip end on the bottom 2a side). Furthermore, the shape of the plunger 4 should also follow that of the syringe barrel 2, for example the cross-sectional shape should be circular.

The gasket 5 is fitted to the first end of the plunger 4 by interlocking, screwing or bonding, and the outer peripheral surface thereof makes contact with the inner wall surface of the syringe barrel 2 in order to provide a state of airtightness between the through-hole in the puncture needle 1, the tubular part 2b which communicates with this through-hole, and the inside of the syringe barrel 2. Furthermore, an orifice (the orifice 5a shown in FIG. 3) for providing communication between the inside of the plunger 4 and the inside of the syringe barrel 2 is formed in the gasket 5. The diameter of the orifice 5a should be narrower than the diameter of the internal flow path of the plunger 4, as shown in FIG. 3. No particular limitation is imposed as to the diameter of the orifice 5a, but it should be set at a diameter such that changes in pressure are readily produced in the syringe barrel 2 and plunger 4 by the pushing and pulling action of the plunger 4. If the diameter of the orifice 5a is narrower than the diameter of the internal flow path of the plunger 4, changes in pressure are readily produced, and the speed of the fluid flowing into the plunger 4 can be increased.

It should be noted that the gasket 5 may be formed as a single piece with the plunger 4. Furthermore, no particular limitation is imposed as to the material from which the gasket 5 is made, but an elastic material, for example an elastomer such as rubber or a synthetic resin should be used because of the contact with the inner wall surface of the syringe barrel 2. Furthermore, the diameter of the orifice 5a in the gasket 5 and the diameter of the first end of the plunger 4 do not both have to be narrower than the diameter of the internal flow path of the plunger 4, and only one of them may be narrower.

The return flow prevention mechanism, shown in FIG. 3 as check valve 6, is detachably fitted to the second end of the plunger 4 (the tip end on the opposite side to the bottom 2a) by interlocking or screwing in such a way as to communicate with the inside of the plunger 4, and allows the fluid flowing into the plunger 4 to flow only in a specified direction. The check valve 6 serves as the return-flow prevention mechanism, and only allows the flow of fluid in an outward direction from the inside of the plunger 4 in accordance with a preset opening pressure value. The example described in this mode of embodiment involves the use of a check valve 6 which is one example of a return-flow prevention mechanism, but this is not limiting and another means may be used as the return-flow prevention mechanism provided that the pressure at which fluid is allowed to pass can be adjusted (the opening pressure value can be adjusted). As shown in FIG. 3, the valve body 6a of the check valve 6 is housed inside a check valve housing (housing) 6b.

It should be noted that an example is given in this mode of embodiment in which the check valve 6 is fitted to the second end of the plunger 4, but the position where the check valve 6 is fitted is not limited to the second end of the plunger 4, and it goes without saying that it can demonstrate a function as a check valve 6 provided that it is fitted to some part of the plunger 4. Furthermore, the opening pressure value of the check valve 6 should be set in accordance with the fluid which is to be measured. For example, if the flow of arterial blood is to be allowed, the opening pressure value of the check valve 6 should be set at around 15-50 mmHg, and preferably at around 30 mmHg. In addition, no particular limitation is imposed as to the type of valve body 6a or check valve 6, and the type may be selected according to use.

The adapter 3 is hollow and serves to connect the puncture needle 1 and syringe barrel 2. An example is shown in FIG. 1 of a case in which the adapter 3 is only configured to connect the puncture needle 1 and syringe barrel 2, but it may have another configuration which branches in two at one end. That is to say, the configuration and attachment/detachment of the adapter 3 may be determined according to the use of the syringe 100.

The operating part 7 is provided at one end of the check valve 6 (the end which is not on the plunger 4 side), and it serves to assist in pushing and pulling operations of the plunger 4. The operating part 7 should therefore be formed so as to project in the outer peripheral direction in order to assist in pushing and pulling operations of the plunger 4 which are carried out by a practitioner. Furthermore, at least one orifice is preferably formed in the operating part 7 so that the flow passage of the check valve 6 is not closed off by the operating part 7. One or more orifices in operating part 7 may be positioned through a top or side surface of operating part 7. It should be noted that the operating part 7 may be formed as a single piece with the check valve 6, or it may be fitted to the check valve 6 as a component which is separate from the check valve 6.

The technique (operation) described herein relates to use of the syringe 100 in order to puncture a vein lying deep in the body and confirming the blood vessel. In this instance, an example will be described in which the catheter is made indwelling by means of the Seldinger technique. A brief description will first be given of the Seldinger technique.

The practitioner first of all estimates where the blood vessel in which the catheter is to be inserted runs, using his or her anatomical knowledge and experience, and then produces an image of the position of the puncture, the direction of the puncture and the depth of the puncture, etc. Then, based on the content of the image, the practitioner makes a puncture through the skin towards a deep part of the body while the puncture needle 1 of the syringe 100 is connected to the syringe barrel 2. At this point, the practitioner pulls the plunger 4 immediately after the tip end of the puncture needle 1 has passed through the skin, producing negative pressure inside the syringe barrel 2 and the puncture needle 1, and with this state maintained advances the puncture needle 1 into the body. This is carried out because the return flow of blood to the syringe barrel can be achieved more quickly and reliably.

In actual fact, the blood pressure in veins lying deep in the body (the subclavian vein or internal jugular vein, for example) is around 2-8 mmHg. It is often the case that it is only possible to achieve blood pressure which is lower than atmospheric pressure, depending on the condition of the patient in whom the catheter is to be made indwelling. In view of this, an operation is required in which the plunger 4 is pulled to produce negative pressure inside the syringe barrel 2 and puncture needle 1 in order to forcibly create a return flow of blood into the syringe barrel 2. Because this operation is carried out, the inside of the syringe barrel 2 and puncture needle 1 must be airtight (at least to the extent that a return flow of blood can be produced).

The operation to confirm the blood vessel is carried out until the intended blood vessel is confirmed. Once the practitioner has seen the return flow of blood in the syringe barrel 2, he or she judges that the puncture needle 1 is positioned inside a blood vessel. If this blood vessel is the intended blood vessel for insertion of the catheter, the practitioner inserts a guidewire into the blood vessel through the puncture needle 1 from which the syringe barrel 2 has been removed, for example. It should be noted that when the Seldinger technique is used to make a catheter indwelling, an adapter 3 having the side port 9 may be used, and the guidewire or catheter may be inserted through the side port 9.

The practitioner then inserts a dilator along the guidewire to dilate the blood vessel into which the catheter is to be inserted. Once the blood vessel has been dilated, the practitioner removes the dilator and then inserts the catheter into the blood vessel over the guidewire. Once the catheter has been inserted at the intended position, the practitioner removes the guidewire. The air inside the catheter is then purged and the catheter is fixed, after which the operation to make the catheter indwelling is complete. It should be noted that it is normal practice to clean the inside of the catheter and to confirm whether the catheter is indwelling in the correct position using X-ray photography or the like.

The method for identifying the blood vessel using the syringe 100 will be described. That is to say, a description will be given of how to establish whether the blood vessel which has been punctured is the target blood vessel. It should be noted that in this instance the opening pressure value of the check valve 6 is set at around 15-50 mmHg to allow the flow of arterial blood.

Determining Vein Access

The practitioner advances the puncture needle deep into the body while there is negative pressure inside the syringe barrel 2, puncture needle 1 and plunger 4. The tip end of the puncture needle 1 is inserted into the blood vessel, while at the same time a return flow of blood can be seen inside the puncture needle 1 and syringe barrel 2 if the needle is inside a vein. The practitioner can therefore recognize that the puncture needle 1 has pierced the intended vein and is correctly placed.

When this has been done and the vein has been pierced by the puncture needle 1, the pressure of the venous blood is lower than the preset opening pressure value of the check valve 6, and therefore there is a return flow of blood into the syringe barrel 2, but the blood column does not rise any further (it only rises as far as the region of the gasket 5, for example). That is to say, the plunger 4 is pulled in order to produce negative pressure inside the syringe barrel 2, puncture needle 1 and plunger 4, and therefore the return flow of blood can be seen, but the check valve 6 does not open and the air inside the plunger 4 remains, so the blood column does not rise any further.

Determining Artery Access

When the puncture needle 1 has pierced an artery, the arterial blood pressure is higher than the preset opening pressure value of the check valve 6, and therefore there is a return flow of blood into the syringe barrel 2, and the blood column rises up into the plunger 4. That is to say, the plunger 4 is pulled in order to produce negative pressure inside the syringe barrel 2 and puncture needle 1, and therefore the return flow of blood can be seen, while the check valve 6 also opens, and the air inside the plunger 4 is pushed outside, so the blood column rises up into the plunger 4. The plunger 4 is clear, that is to say completely or partially transparent or translucent, and therefore the practitioner can visually confirm whether the blood column has risen up into the plunger 4. Furthermore, third parties (auxiliary staff such as physicians other than the practitioner, for example) are also able to observe the state inside the plunger 4.

In this way, the practitioner can establish, in a short time and with accuracy, whether the blood vessel which has been punctured is the intended blood vessel, immediately after the return flow of blood has been confirmed. If the intended blood vessel is a vein but it is confirmed that the blood vessel which has been punctured is an artery, the practitioner can immediately halt the puncture and quickly take suitable action to deal with the situation. This means that if the syringe 100 is used in a catheter set, it is possible to adopt a more usable and practical technique. The burden on the patient is also lightened.

As seen above, the syringe 100 comprises the hollow plunger 4 and check valve 6, and therefore it is possible to qualitatively visualize the pressure of the fluid by using the difference in pressure between fluids such as blood, and it is possible to establish, in a short time and with accuracy, that the target has been pierced by the puncture needle 1. With this syringe 100, it is possible to establish that the target has been pierced by the puncture needle 1 using the same operation as with a conventional commercial syringe which does not have the function of the syringe 100, in other words using an operation which does not require any new technique at all. Accordingly, the syringe 100 does not require a complex structure or operation, and makes it possible to carry out simple operations to identify fluids using exactly the same puncture technique as with a conventional syringe, and therefore it is easy to use and more practical.

Furthermore, even if it is not possible to puncture the target in a single operation with the syringe 100, a second operation, and subsequent operations, can be carried out simply by pushing the plunger 4 to discharge the fluid which has flowed back into the syringe barrel 2. In addition, the syringe 100 makes use of the function of the conventional check valve 6, and therefore it does not require a complex structure or operation, and the target can be identified in a short time and with accuracy.

In addition, the syringe 100 can be produced at roughly the same size as a conventional commercial syringe which does not have the function of the syringe 100. That is to say, the syringe 100 makes it possible to qualitatively visualize the pressure of a fluid simply by having the hollow plunger 4 and the check valve 6 fitted at the end of the plunger 4, and therefore it can be endowed with roughly the same diameter as a conventional syringe and can respond to the need for compactness. In addition, the check valve 6 which is used may be a standard check valve, and therefore this leads to reduced costs.

Figure 4:
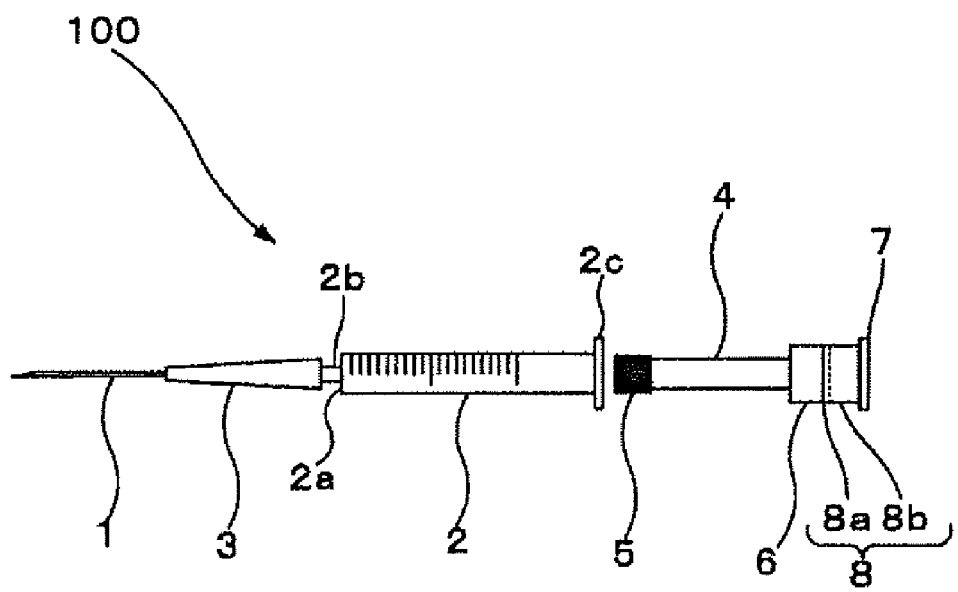
FIG. 4 is a schematic showing another example of the structure of the syringe according to a mode of embodiment of the present invention.

FIG. 4 is a schematic showing another example of the structure of the syringe 100. This other example of the structure of the syringe 100 will be described in conjunction with FIG. 4. This syringe 100 is provided with a filter part 8 downstream of the check valve 6, in other words at the end of the check valve 6 opposite the plunger 4 side. This filter part 8 has a filter 8a which is housed inside a filter housing 8b. The filter 8a consists of a hydrophobic filter which does not allow the passage of liquid while allowing the passage of gas. It should be noted that the rest of the structure is the same as in the syringe 100 described in relation to FIGS. 1 to 3. Furthermore, when the filter part 8 is provided, the operating part 7 may be formed as a single piece with the filter part 8, or it may be attached to the filter part 8 as a separate component to the filter part 8. In addition, the filter part 8 may be provided on the operating part 7.

When the filter 8a is provided downstream of the check valve 6, the liquid which has risen into the plunger 4 can be blocked. For example, when the puncture needle 1 has punctured an artery, the blood may flow back into the plunger 4 with force, passing through the check valve 6 and leaking outside. If a patient suffering from an infectious disease is undergoing treatment, the leaked blood constitutes an undesirable presence for the medical staff around the patient, including the practitioner. It is possible to prepare for this kind of situation by providing the filter 8a. Health and safety requirements can therefore be satisfied by providing the filter 8a.

It should be noted that an example has been described in the modes of embodiment in which the target which is punctured by the puncture needle 1 is a blood vessel, but this is not limiting, and provided that a difference in pressure can be utilized, this may be used as a target. In this case, the opening pressure value of the check valve 6 should be set in accordance with the target. Furthermore, an example has been described in the modes of embodiment in which a catheter is made indwelling using the syringe 100 by means of the Seldinger technique, but this is not limiting, and the syringe 100 can equally be used with a method to make a catheter indwelling which does not employ a guide wire (the "through-the-cannula" technique, for example). In addition, the syringe 100 may equally be used when a dialysis catheter or a catheter introducer for the heart etc., for example, is made indwelling, as well as in the case of a central venous catheter.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

| Key to Symbols | |
|---|---|
| 1 | puncture needle |
| 2 | syringe barrel |
| 2a | bottom |
| 2b | tubular part |
| 2c | stopper |
| 3 | adapter |
| 4 | plunger |

-continued

Key to Symbols

| | |
|---|---|
| 5 | gasket |
| 5a | orifice |
| 6 | check valve |
| 6a | valve body |
| 6b | check valve housing |
| 7 | operating part |
| 8 | filter part |
| 8a | filter |
| 8b | filter housing |
| 100 | syringe |

What is claimed is:

1. A syringe, comprising:
a clear syringe barrel having a first bottom end having a throughhole, a second end, and defining a barrel cavity therebetween;
a clear plunger slidably disposed within the syringe cavity, the plunger rod comprising a first end having a first orifice, a second end having a second orifice, and defining a plunger cavity therebetween;
a gasket positioned on the first end of the plunger, extending into the barrel cavity, and contacting an interior surface of the barrel cavity, the gasket comprising an orifice fluidly connected to the barrel cavity and the plunger cavity; and
a return-flow prevention mechanism positioned at the second end of the plunger thereby allowing fluid flowing into the plunger from the first end of the plunger to flow in an outward direction from the inside of the plunger, the return-flow prevention mechanism being constructed to permit fluid to flow past the mechanism and out of the plunger in response to fluid pressure acting on the mechanism from within the plunger.

2. The syringe according to claim 1, wherein an opening fluid pressure value of the return-flow prevention mechanism is set in accordance with the fluid flowing into the plunger.

3. The syringe according to claim 2, wherein the return-flow prevention mechanism comprises a check valve comprising a valve body and a housing in which the valve body is housed, and is detachably fitted to the second end of the plunger with the housing interposed.

4. The syringe according to any one of claim 1, further comprising a puncture needle comprising a fluid inflow port detachably fitted to the bottom end of the syringe barrel.

5. The syringe according to claim 3, further comprising a hydrophobic filter positioned downstream of the return-flow prevention mechanism.

6. The syringe according to claim 1, wherein the first orifice of the plunger rod has a diameter smaller than a diameter of the plunger cavity.

7. The syringe according to claim 1, wherein the orifice of the gasket has a diameter smaller than a diameter of the barrel cavity.

8. The syringe according to claim 7, wherein the orifice of the gasket has a diameter smaller than a diameter of the plunger cavity.

9. A catheter set comprising:
a catheter and a syringe, the syringe comprising:
a clear syringe barrel having a first bottom end having a throughhole, a second end, and defining a barrel cavity therebetween;
a clear plunger slidably disposed within the syringe cavity, the plunger rod comprising a first end having a first orifice, a second end having a second orifice, and defining a plunger cavity therebetween;
a gasket positioned on the first end of the plunger, extending into the syringe cavity, and contacting an interior surface of the barrel cavity, the gasket comprising an orifice fluidly connected to the barrel cavity and the plunger cavity; and
a return-flow prevention mechanism positioned on the second end of the plunger thereby allowing fluid flowing into the plunger from the first end of the plunger to flow in an outward direction from the inside of the plunger, the return-flow prevention mechanism being constructed to permit fluid to flow past the mechanism and out of the plunger in response to fluid pressure acting on the mechanism from within the plunger.

10. The syringe according to claim 2, wherein the opening fluid pressure value of the return-flow prevention mechanism is between about 15 and about 50 mmHg.

11. The syringe according to claim 2, wherein the opening fluid pressure value is about 30 mmHg.

* * * * *